(12) United States Patent
Schmitt

(10) Patent No.: US 8,229,529 B2
(45) Date of Patent: *Jul. 24, 2012

(54) DEVICE AND METHOD FOR MONITORING BODY FLUID AND ELECTROLYTE DISORDERS

(75) Inventor: Joseph M. Schmitt, Andover, MA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1688 days.

This patent is subject to a terminal disclaimer.

(21) Appl. No.: 11/240,927

(22) Filed: Sep. 30, 2005

(65) Prior Publication Data

US 2006/0020181 A1    Jan. 26, 2006

Related U.S. Application Data

(63) Continuation of application No. 10/441,943, filed on May 20, 2003, now Pat. No. 7,236,811, which is a continuation of application No. 09/810,918, filed on Mar. 16, 2001, now Pat. No. 6,591,122.

(51) Int. Cl.
*A61B 5/1455* (2006.01)
(52) U.S. Cl. ...................................................... 600/310
(58) Field of Classification Search .................. 600/310, 600/306, 307, 476, 407, 551; 356/320
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,723,554 A | 2/1988 | Oman et al. |
| 4,805,623 A | 2/1989 | Jobsis |

(Continued)

FOREIGN PATENT DOCUMENTS

CA    2353007 A1    6/2000

(Continued)

OTHER PUBLICATIONS

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

(Continued)

*Primary Examiner* — Tse Chen
*Assistant Examiner* — Elmer Chao
(74) *Attorney, Agent, or Firm* — Fletcher Yoder

(57) ABSTRACT

A device and a method for measuring body fluid-related metrics using spectrophotometry to facilitate therapeutic interventions aimed at restoring body fluid balance. The specific body fluid-related metrics include the absolute volume fraction of water in the extravascular and intravascular tissue compartments, as well as the shifts of water between these two compartments. The absolute volume fraction of water is determined using algorithms where received radiation measured at two or more wavelengths are combined to form either a single ratio, a sum of ratios or ratio of ratios, in which the received radiation in the numerator depends primarily on the absorbance of water and the received radiation in the denominator depends primarily on the absorbance of water and the sum of the absorbances of non-heme proteins, lipids and water in tissue. The difference between the fraction of water in the intravascular fluid volume and extravascular fluid volume compartments are also determined.

51 Claims, 4 Drawing Sheets

U.S. PATENT DOCUMENTS

| | | | |
|---|---|---|---|
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 5,057,695 A | 10/1991 | Hirao et al. | |
| 5,077,476 A * | 12/1991 | Rosenthal | 250/339.04 |
| 5,086,781 A | 2/1992 | Bookspan | |
| 5,111,817 A | 5/1992 | Clark et al. | |
| 5,146,091 A | 9/1992 | Knudson | |
| 5,224,478 A | 7/1993 | Sakai et al. | |
| 5,277,181 A | 1/1994 | Mendelson et al. | |
| 5,279,295 A | 1/1994 | Martens et al. | |
| 5,282,467 A | 2/1994 | Piantadosi et al. | |
| 5,337,745 A | 8/1994 | Benaron | |
| 5,337,937 A | 8/1994 | Remiszewski et al. | |
| 5,348,004 A | 9/1994 | Hollub | |
| 5,355,880 A | 10/1994 | Thomas et al. | |
| 5,365,066 A * | 11/1994 | Krueger et al. | 250/341.2 |
| 5,377,674 A | 1/1995 | Kuestner | |
| 5,499,627 A | 3/1996 | Steuer et al. | |
| 5,615,689 A | 4/1997 | Kotler | |
| 5,687,721 A | 11/1997 | Kuhls | |
| 5,701,902 A * | 12/1997 | Vari et al. | 600/473 |
| 5,720,284 A | 2/1998 | Aoyagi et al. | |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,833,602 A | 11/1998 | Osemwota | |
| 5,853,364 A | 12/1998 | Baker, Jr. et al. | |
| 5,860,919 A | 1/1999 | Kiani-Azarbayjany et al. | |
| 5,906,582 A | 5/1999 | Kondo et al. | |
| 5,933,226 A | 8/1999 | Yamanishi | |
| 6,064,898 A | 5/2000 | Aldrich | |
| 6,125,297 A | 9/2000 | Siconolfi | |
| 6,149,591 A | 11/2000 | Henderson et al. | |
| 6,178,342 B1 | 1/2001 | Thompson et al. | |
| 6,222,189 B1 | 4/2001 | Misner et al. | |
| 6,246,894 B1 | 6/2001 | Steuer et al. | |
| 6,280,381 B1 | 8/2001 | Malin et al. | |
| 6,280,396 B1 | 8/2001 | Clark et al. | |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,442,408 B1 * | 8/2002 | Wenzel et al. | 600/310 |
| 6,466,807 B1 | 10/2002 | Dobson et al. | |
| 6,488,677 B1 | 12/2002 | Bowman et al. | |
| 6,512,936 B1 | 1/2003 | Monfre et al. | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 | 9/2003 | Aldrich | |
| 6,635,491 B1 | 10/2003 | Khalil et al. | |
| 6,636,759 B2 | 10/2003 | Robinson | |
| 6,643,543 B2 | 11/2003 | Takehara et al. | |
| 6,654,620 B2 | 11/2003 | Wu et al. | |
| 6,668,181 B2 | 12/2003 | Wenzel et al. | |
| 6,675,029 B2 | 1/2004 | Monfre et al. | |
| 6,687,519 B2 | 2/2004 | Steuer et al. | |
| 6,777,240 B2 | 8/2004 | Hazen et al. | |
| 6,840,904 B2 | 1/2005 | Goldberg | |
| 6,849,046 B1 | 2/2005 | Eyal-Bickels | |
| 6,873,865 B2 | 3/2005 | Steuer et al. | |
| 6,950,699 B1 | 9/2005 | Manwaring et al. | |
| 6,954,661 B2 | 10/2005 | Cho et al. | |
| 6,961,598 B2 | 11/2005 | Diab | |
| 7,257,433 B2 | 8/2007 | Takamura et al. | |
| 7,283,242 B2 | 10/2007 | Thornton | |
| 7,398,115 B2 | 7/2008 | Stuer et al. | |
| 2001/0020122 A1 | 9/2001 | Steuer et al. | |
| 2003/0060693 A1 | 3/2003 | Monfre et al. | |
| 2004/0127777 A1 | 7/2004 | Richti et al. | |
| 2004/0147034 A1 | 7/2004 | Gore et al. | |
| 2004/0230106 A1 | 11/2004 | Schmitt et al. | |
| 2005/0065415 A1 | 3/2005 | Cho et al. | |
| 2005/0119538 A1 | 6/2005 | Jeon et al. | |
| 2005/0192493 A1 | 9/2005 | Wuori | |
| 2006/0020179 A1 | 1/2006 | Anderson et al. | |
| 2006/0052680 A1 | 3/2006 | Diab | |
| 2006/0122475 A1 | 6/2006 | Balberg et al. | |
| 2006/0167350 A1 | 7/2006 | Monfre et al. | |
| 2006/0247506 A1 | 11/2006 | Balberg et al. | |
| 2006/0253016 A1 | 11/2006 | Baker, Jr. et al. | |

FOREIGN PATENT DOCUMENTS

| | | |
|---|---|---|
| DE | 19855521 A1 | 6/2000 |
| EP | 1135184 A1 | 6/2000 |
| EP | 1184663 A2 | 3/2002 |
| EP | 1491135 | 12/2004 |
| FR | 2710517 | 4/1995 |
| JP | 4-40940 | 2/1992 |
| JP | 5-329163 | 12/1993 |
| JP | 11-244266 | 9/1999 |
| JP | 2004081427 A | 3/2004 |
| WO | WO 95/19562 A | 7/1995 |
| WO | WO 98/34097 | 8/1998 |
| WO | WO 00/32262 A1 | 6/2000 |
| WO | WO 00/71025 A1 | 11/2000 |
| WO | WO 93/13706 A2 | 1/2001 |
| WO | WO 01/16577 A1 | 3/2001 |
| WO | 03010510 A2 | 2/2003 |
| WO | 2005041765 A1 | 5/2005 |

OTHER PUBLICATIONS

Watson, Walter, "Hydration of fat-free body mass: new physiological modeling approach," *Am J. Physiol. Endocrinol. Metab.*, Letters to the Editor, vol. 278, pp. E752-E753 (2001).

Garcia-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

Troy, Tamara L., et al., "Optical properties of human skin in the near infrared wavelength range of 1000 to 2200nm," Journal of Biomedical Optics, vol. 6, No. 2, pp. 167-176 (Apr. 2001).

Attas, E. Michael, et al., "Near-IR Spectroscopic Imaging for Skin Hydration: The Long and the Short of It," Biopolymers, vol. 67, No. 2, pp. 96-106 (2002).

Attas, M. et al., "Long-Wavelength Near-Infrared Spectroscopic Imaging for In-Vivo Skin Hydration Measurements," Vibrational spectroscopy (Feb. 28, 2002), vol. 28, No. 1, p. 37-43.

Blank, T.B., et al., "Clinical Results from a Non-Invasive Blood Glucose Monitor," Photonics West 2002 Meeting, San Jose, California, Jan. 19-25, 2002 (25 pages).

Chamney, Paul W., et al., "A new technique for establishing dry weight in hemodialysis patients via whole body bioimpedance," Kidney International, vol. 61, pp. 2250-2258 (2002).

Drobin, Dan, et al., "Kinetics of Isotonic and Hypertonic Plasma Volume Expanders," Anesthesiology, vol. 96, No. 6, pp. 1371-1380 (Jun. 2002).

Endo, Yutaka, et al., "Changes in Blood Pressure and Muscle Sympathetic Nerve Activity during Water Drinking in Humans," Japanese Journal of Physiology, vol. 52, pp. 421-427 (2002).

Haga, Henning A., et al., "Motor responses to stimulation during isoflurane anaesthesia in pigs," Veterinary Anaesthesia and Analgesia, vol. 29, pp. 69-75 (2002).

Klaus, Stephan, et al., "Assessment of fluid balance by measurement of skin tissue thickness during clinical anaesthesia," Clin. Physiol. & Func. Im., vol. 22, pp. 197-201 (2002).

Meglinski, Igor V., et al., "Quantitative assessment of skin layers absorption and skin reflectance spectra simulation in the visible and near-infrared spectral regions," Physiol. Meas., vol. 23, pp. 741-753, (2002).

Perez-de-Sá, Valéria, et al., "Mild Hypothermia Has Minimal Effects on the Tolerance to Severe Progressive Normovolemic Anemia in Swine," Anesthesiology, Vo. 97, pp. 1189-1197 (2002).

Ponec, Maria, et al., "Charactrization of Reconstructed Skin Models," Skin Pharmacol Appl Skin Physiol., vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," Skin Research and Technology, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," Anesthesiology, vol. 97, No. 3, pp. 660-670 (Sep. 2002).

Wong, William W., et al., "Evaluating body fat in girls and female adolescents: advantages and disadvantages of dual-energy X-ray absorptiometry," Am J. Clin Nutr., vol. 76, pp. 384-389 (2002).

Baković, Darija, et al., "Spleen volume and blood flow response to repeated breath-hold apneas," J. Appl. Physiol., vol. 95, pp. 1460-1466 (2003).

Bartok, Cynthia, et al., "Measurement of nutritional statusin simulated microgravity by bioelectrical impedance spectroscopy," J. Appl. Physiol., vol. 95, pp. 225-232 (2003).

Bouwstra, Joke A., et al., "Water Distribution and Related Morphology in Human Stratum Corneum at Different Hydration Levels," J. Invest Dermatol, vol. 150, pp. 750-758 (2003).

Butte, Nancy F., et al., "Composition of gestational weight gain impacts maternal fat retention and infant birth weight," Am J. Obstet Gynecol, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," The Journal of Trauma, Injury, Infection, and Critical Care, vol. 54, No. 5, pp. S20-S25 (May Supplement 2003).

Cook, Lynda S., "IV Vluid Resuscitation," Journal of Infusion Nursing, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," European Journal of Clinical Nutrition, vol. 57, pp. 909-916 (2003).

Farstad, M., et al., "Fluid extravasation during cardiopulmonary bypass in piglets—effects of hypothermia and different cooling protocols," Acta Anaesthesiol. Scand., vol. 47, pp. 397-406 (2003).

Grandjean et al., "Hydration: issues for the 21st century", Nutrition Reviews, 61(8):261-271 (2003).

Heise, H.M., et al., "Reflectance spectroscopy can quantify cutaneous haemoglobin oxygenation by oxygen uptake from the atmosphere after epidermal barrier distruption," Skin Research and Technology, vol. 9, pp. 295-298 (2003).

Kasemsumran, Sumaporn, et al., "Simultaneous determination of human serum albumin, ☐-globulin, and glucose in a phosphate buffer solution by near-infrared spectroscopy with moving window partial least-squares regression," Analyst, vol. 128, pp.-1471-1477 (2003).

Kemming, G.I., et al., "Hyperoxic ventilation at the critical haematocrit," Resuscitation, vol. 56, pp. 289-297 (2003).

Kurita, T., et al., "Comparison of isoflurane and propofol-fentanyl anaesthesia in a swine model of asphyxia," British Journal of Anaesthesia, vol. 91, No. 6, pp. 871-877 (2003).

Laaksonen, DE, et al., "Changes in abdominal subcutaneous fat water content with rapid weight loss and long-term weight maintenance in abdominally obese men and women," International Journal of Obesity, vol. 27, pp. 677-683 (2003).

Mao, Jinshu, et al., "Study of Novel Chitosan-gelatin artificial skin in vitro," J. Miomed Mater Res., vol. 64, Part A, pp. 301-308 (2003).

Mauran, P., et al., "Renal and hormonal responses to isotonic saline infusion after 3 days' dead-down tilt vs. supine and seated positions," Acta Physiol. Scand., vol. 177, pp. 167-176, (2003).

McHugh, Gerard, "Letter—Passive leg elevation and head-down tilt: effects and duration of changes," Critical Care, vol. 7, No. 3, p. 246 (Jun. 2003).

Meglinski, I.V., et al., "Computer simulation of the skin reflectance spectra," Computer Methods and Programs in Biomedicine, vol. 70, pp. 179-186, (2003).

Mendelsohn, Richard, et al., "Infrared microspectroscopic imaging maps the spatial distribution of exogenous molecules in skin," Journal of Biomedical Optics, vol. 8, No. 2, pp. 185-190 (Apr. 2003).

Mentes, Janet C., et al., "Reducing Hydration=-Linked events in Nursing Home Residents," Clinical Nursing Research, vol. 12, No. 3, pp. 210-225 (Aug. 2003).

Merritt, Sean, et al., "Coregistration of diffuse optical spectroscopy and magnetic resonance imaging in a rat tumor model," Applied Optics, vol. 42, No. 16, pp. 2951-2959 (Jun. 2003).

Parker, Lisa, et al., "Validity of Six Field and Laboratory Methods for Measurement of Body Composition in Boys," Obesity Research, vol. 11, No. 7, pp. 852-858 (Jul. 2003).

Petäjä L., et al., "Dielectric constant of skin and subcutaneous fat to assess fluid changes after cardiac surgery", Physiological Measurement, 24: 3383-390, (2003).

Richardson, Andrew D., et al., "Multivariate analyses of visible/near infrared (VIS/NIR) absorbance spectra reveal underlying spectral differences among dried, ground confier needle samples from different growth environments," New Phytologist, vol. 161, pp. 291-301 (2003).

Robinson, Martin P., et al., "A novel method of studying total body water content using a resonant cavity: experiments and numerical simulation," Phys. Med. Biol., vol. 48, pp. 113-125, (2003).

Sergi, Giuseppe, et al., "Changes in Fluid Compartments and Body Composition in Obese Women after Weight Loss Induced by Gastric Banding," Ann. Nutr Metab., vol. 47., pp. 152-157 (2003).

Windberger, U, et al., "Whole blood viscosity, plasma viscosity and erythrocyte aggregation in nine mammalian species; reference values and comparison of data," Exp., Physiol., vol. 88, No. 3, pp. 431-440 (2003).

Wolf, Martin, et al., "Absolute Frequency-Domain pulse Oximetry of the Brain: Methodology and Measurements," Oxygen Transport to Tissue XXIV, Chapter 7, Dunn and Swartz, Kluwer Academic/Plenum Publishers, pp. 61-73 (2003).

J. H. Ali, et al.; "Near Infrared Spectroscopy and Imaging to Prove differences in Water content in normal and Cancer Human Prostate Tissues," Technology in Cancer Research & Treatment, vol. 3, No. 5, pp. 491-497 (Oct. 2004).

Arimoto et al., "Non-contact skin moisture measurement based on near-infrared spectroscopy", Applied Spectroscopy, 58(12):1439-1445 (2004).

Wheeler, Owen H., "Near Infrared Spectra of Organic Compounds," Department of Chemistry, College of Agriculture and Mechanic Arts, University of Puerto Rico (Mar. 1929).

Pace, Nello, et al., "Studies on Body Composition: III. The body water and chemically combined nitrogen content in relation to fat content," Naval Medical Research Institute, Bethesda, Maryland (Jan. 11, 1945).

Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).

Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).

Goldstein, R., et al., "The Near-Infrared Absorption of Liquid Water at Temperatures Between 27 and 209° C," *J. Quant. Spectrosc. Radiat. Transfer.*, vol. 4, pp. 441-451 (1964).

Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).

Houseman, R.A., et al., "The measurement of total body water in living pigs by deuterium oxide dilution and its relation to body composition," *Br. J. Nutr.*, vol. 30, pp. 149-156 (1973).

Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).

Lesser, G.T., et al., "Body water compartments with human aging using fat-free mass as the reference standard," *Am J. Physiol Regul Integr Comp Physiol.*, vol. 236, pp. 215-220 (1979).

Sheng, Hwai-Ping, et al., "A review of body composition studies with emphasis on total body water and fat," *The American Journal of Clinical Nutrition*, vol. 32., pp. 630-647 (Mar. 1979).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J., et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," *Journal of Food Science*, vol. 48, pp. 471-474 (1983).

Martens, Harald, et al., "Understanding food research data," Food Research and Data Analysis, Applied Science Publishers, pp. 5-38 (1983).

Shields, R. G., Jr., et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Cohn, S.H., et al., "Assessment of cellular mass and lean body mass by noninvasive nuclear techniques," *J. Lab Clin Med.*, vol. 105, pp. 305-311 (1985).

Hannon, John P., et al., "Splenic red cell sequestration and blood volume measurements in conscious pigs," *Am J. Physiol.*, vol. 248, pp. R293-R301 (1985).

Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Cox, Patrick, et al., "Variations in Lipids in Different Layers of Porcine Epidermis," *J. Invest Dermatol.*, vol. 87, pp. 741-744 (1986).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Hedberg, Chrisopher L., et al., "The Time Course of Lipid Biosynthesis in Pig Epidermis," *J. Invest Dermatol.*, vol. 91, pp. 169-174 (1988).

Hedberg, Christopher L., et al., "The nonpolar Lipids of Pig Epidermis," *J. Invest Dermatol.*, vol. 90, pp. 225-229 (1988).

Trapp, Scott A., et al., "An improved spectrophotometric bromide assay for the estimation of extracellular water volume," *Clinica Chimica Acta*, vol. 181, pp. 207-212, (1989).

Bommannan, D., et al., "Examination of Stratum Corneum Barrier Function In Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.

Mak, Vivien H.W., et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$-, $\beta$- and $\kappa$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M., et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of comified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-4272.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging *versus* Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to. Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "Perspectives—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume In Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M-380 (2001).

Divert, Victor E., "Body Thermal State Influence on Local Skin Thermosensitivity," *International Journal of Circumpolar Health*, vol. 60, pp. 305-311 (2001).

Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki, et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G., et al., "Unreliable use of standard muscle hydration value in obesity," *Am J. Physiol Endocrinal Metab.*, vol. 280, pp. E365-371, (2001).

Ritz, Patrick, "Chronic Cellular Dehydration in the Aged Patient," Journal of Gerontology, vol. 56A, No. 6, pp. M349-M352 (2001).

Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

\* cited by examiner

DEVICE AND METHOD FOR MONITORING BODY FLUID AND ELECTROLYTE DISORDERS

CROSS-REFERENCES TO RELATED APPLICATIONS

This application is a continuation of U.S. patent application Ser. No. 10/441,943, filed on May 20, 2003, which is a continuation of U.S. patent application Ser. No. 09/810,918, filed on Mar. 16, 2001, now U.S. Pat. No. 6,591,122, the full disclosures of which are incorporated herein by reference.

BACKGROUND OF THE INVENTION

The maintenance of body fluid balance is of foremost concern in the care and treatment of critically ill patients, yet physicians have access to few diagnostic tools to assist them in this vital task. Patients with congestive heart failure, for example, frequently suffer from chronic systemic edema, which must be controlled within tight limits to ensure adequate tissue perfusion and prevent dangerous electrolyte disturbances. Dehydration of infants and children suffering from diarrhea can be life-threatening if not recognized and treated promptly.

The most common method for judging the severity of edema or dehydration is based on the interpretation of subjective clinical signs (e.g., swelling of limbs, dry mucous membranes), with additional information provided by measurements of the frequency of urination, heart rate, serum urea nitrogen SUN/creatinine ratios, and blood electrolyte levels. None of these variables alone, however, is a direct and quantitative measure of water retention or loss.

The indicator-dilution technique, which provides the most accurate direct measure of water in body tissues, is the present de facto standard for assessment of body fluid distribution. It is, however, an invasive technique that requires blood sampling. Additionally, a number of patents have disclosed designs of electrical impedance monitors for measurement of total body water. The electrical-impedance technique is based on measuring changes in the high-frequency (typically 10 KHz-1 MHz) electrical impedance of a portion of the body. Mixed results have been obtained with the electrical-impedance technique in clinical studies of body fluid disturbances as reported by various investigators. The rather poor accuracy of the technique seen in many studies point to unresolved deficiencies of these designs when applied in a clinical setting.

Therefore, there exists a need for methods and devices for monitoring total body water fractions which do not suffer from problems due to their being invasive, subjective and inaccurate.

SUMMARY OF THE INVENTION

Embodiments of the present invention provide devices and methods that measure body fluid-related metrics using spectrophotometry to facilitate therapeutic interventions aimed at restoring body fluid balance. The specific body fluid-related metrics include the absolute volume fraction of water in the extravascular and intravascular tissue compartments, as well as the shifts of water between these two compartments. The absolute volume fraction of water is determined using algorithms where received radiation measured at two or more wavelengths are combined to form either a single ratio, a sum of ratios or ratio of ratios of the form $\log [R(\lambda_1)/R(\lambda_2)]$ in which the received radiation in the numerator depends primarily on the absorbance of water and the received radiation in the denominator depends primarily on the absorbance of water and the sum of the absorbances of non-heme proteins and lipids in tissue.

The difference between the fraction of water in the intravascular fluid volume ("IFV") and extravascular fluid volume ("EFV") compartments are also determined using a differential method that takes advantage of the observation that pulsations caused by expansion of blood vessels in the skin, as the heart beats, produce changes in the received radiation at a particular wavelength that are proportional to the difference between the effective absorption of light in the blood and the surrounding tissue. This difference, integrated over time, provides a measure of the quantity of the fluid that shifts into and out of the capillaries. A mechanism for mechanically inducing a pulse is built into the device to improve the reliability of measurements of IFV-EFV under weak-pulse conditions.

For a fuller understanding of the nature and advantages of the embodiments of the present invention, reference should be made to the following detailed description taken in conjunction with the accompanying drawings.

DESCRIPTION OF THE SPECIFIC EMBODIMENTS

Figure 1:
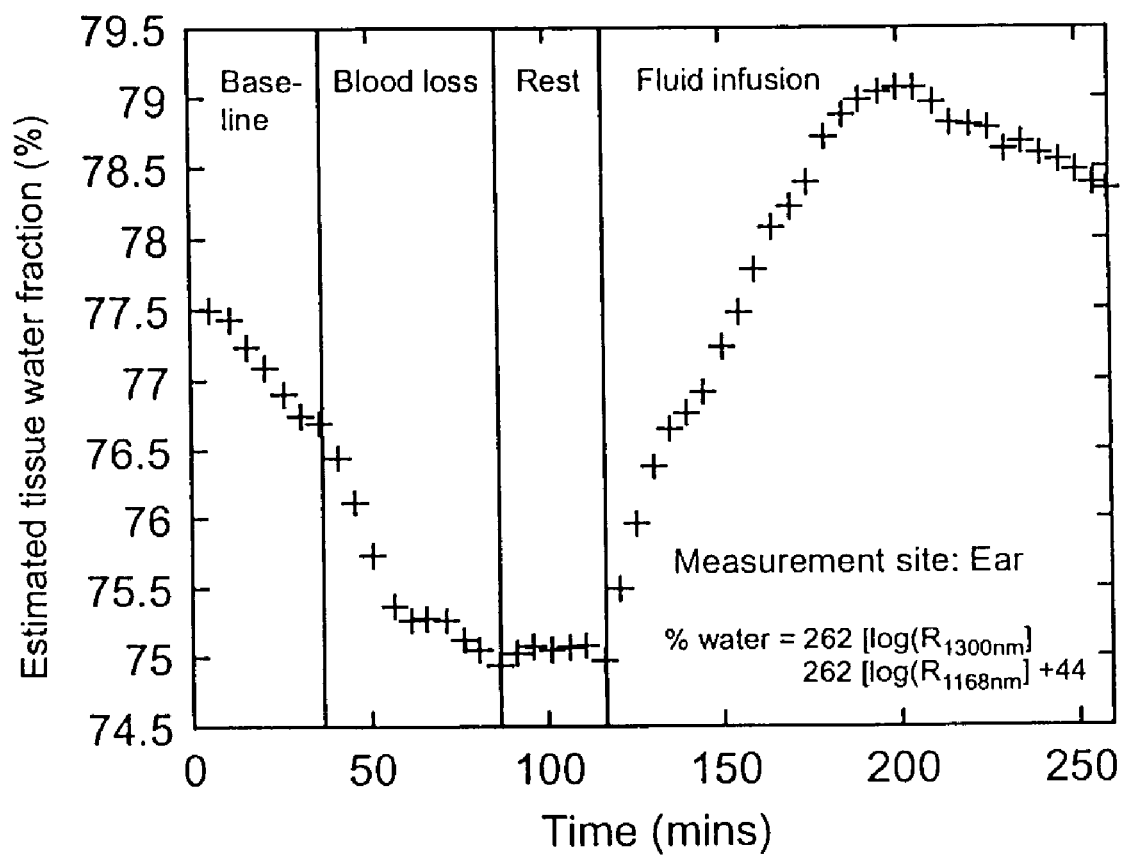
FIG. 1 is a graph showing tissue water fraction measured on the ear of a pig during an experiment using reflectance measurements at two wavelengths.

Embodiments of the present invention overcome the problems of invasiveness, subjectivity, and inaccuracy from which previous methods for body fluid assessment have suffered. The method of diffuse reflectance near-infrared ("NIR") spectroscopy is employed to measure the absolute fraction of water in skin. An increase or decrease in the free (non protein-bound) water content of the skin produces unique alterations of its NIR reflectance spectrum in three primary bands of wavelengths-(1100-1350 nm, 1500-1800 nm, and 2000-2300 nm) in which none-heme proteins (primarily collagen and elastin), lipids, and water absorb. According to the results of numerical simulations and experimental studies carried out by the inventor, the tissue water fraction $f_w$, defined spectroscopically as the ratio of the absorbance of water and the sum of the absorbances of none-heme proteins, lipids, and water in the tissue, can be measured accurately in the presence of nonspecific scattering variation, temperature, and other interfering variables.

In embodiments of this invention, the apparatus and its associated measurement algorithm are designed according to the following guidelines:

1. To avoid the shunting of light through the superficial layers of the epidermis, the light source and detector in optical reflectance probe have low numerical apertures, typically less than 0.3.
2. The spacing between the source and detector in the probe is in the range of 1-5 mm to confine the light primarily to the dermis.
3. The reflectances are measured at wavelengths greater than 1150 nm to reduce the influence of hemoglobin absorption.
4. To ensure that the expression that relates the measured reflectances and $f_w$ yields estimates of water fraction that are insensitive to scattering variations, the lengths of the optical paths through the dermis at the wavelengths at which the reflectances are measured are matched as closely as possible. This matching is achieved by judicious selection of wavelength sets that have similar water absorption characteristics. Such wavelength sets may be selected from any one of the three primary wavelength bands (1100-1350 nm, 1500-1800 nm, and 2000-2300 nm) discussed above. Wavelength pairs or sets are chosen from within one of these three primary bands, and not from across the bands. More particularly the wavelength pair of 1180 and 1300 nm are one such wavelength set where the lengths of the optical paths through the dermis at these wavelengths are matched as closely as possible.
5. To ensure that the expression that relates the measured reflectances and $f_w$ yields estimates of water fraction that are insensitive to temperature variations, the wavelengths at which the reflectances are measured are chosen to be either close to temperature isosbestic wavelengths in the water absorption spectrum or the reflectances are combined in a way that cancels the temperature dependencies of the individual reflectances. Typically, absorption peaks of various biological tissue components may shift with variations in temperature. Here, wavelengths are selected at points in the absorption spectrum where no significant temperature shift occurs. Alternately, by knowing the value of this temperature shift, wavelength sets may be chosen such that any temperature shift is mathematically canceled out when optical measurements are combined to compute the value of a tissue water metric. Such wavelength sets may be selected from any one of the three primary wavelength bands (1100-1350 nm, 1500-1800 nm, and 2000-2300 nm) discussed above. Wavelength pairs or sets are chosen from within one of these three primary bands, and not from across the bands. More particularly the wavelength pair of 1180 and 1300 nm are one such pair of temperature isosbestic wavelengths in the water absorption spectrum.
6. The reflectances measured at two or more wavelengths are combined to form either a single ratio, a sum of ratios or ratio of ratios of the form $\log [R(\lambda_1)/R(\lambda_2)]$ in which the reflectance in the numerator depends primarily on the absorbance of water and the reflectance in the denominator is nearly independent of the fraction of solids (lipids and proteins) in the tissue.

Thus, in one embodiment of the present invention the water fraction, $f_w$ is estimated according to the following equation, based on the measurement of reflectances, $R(\lambda)$ at two wavelengths and the empirically chosen calibration constants $c_0$ and $c_1$:

$$f_w = c_1 \log [R(\lambda_1)/R(\lambda_2)] + c_0 \qquad (1)$$

Numerical simulations and in vitro experiments indicate that $f_w$ can be estimated with an accuracy of approximately ±2% over a range of water contents between 50 and 80% using Equation (1), with reflectances $R(\lambda)$ measured at two wavelengths and the calibration constants $c_0$ and $c_1$ chosen empirically. Examples of suitable wavelength pairs are $\lambda_1=1300$ nm, $\lambda_2=1168$ nm, and $\lambda_1=1230$ nm, $\lambda_2=1168$ nm.

The ability to measure changes in the water content in the ear of a pig using two-wavelength NIR reflectometry was demonstrated experimentally in a study in which a massive hemorrhage was induced in a pig and the lost blood was replaced with lactated Ringer's solution over a period of several hours. Ringer's solution is a well-known solution of salts in boiled and purified water. FIG. 1 shows the water fraction in the skin of the ear of a pig, measured using Equation (1) with $\lambda_1=1300$ nm and $\lambda_2=1168$ nm. Referring to FIG. 1, it should be noted that experimental observations of concern to this embodiment commence when the lactated Ringer's solution was infused 120 minutes after the start of the experiment. It should also be noted that the drift in the water fraction from approximately 77.5% to 75% before the infusion is not related to this infusion experiment, but is related to the base-line hemorrhage portion of the experiment. The results show that the method of the present embodiment correctly reflects the effect of the infusion by showing an increase in tissue water fraction from approximately 75% to 79% while the infusion is continuing. These data suggest that the disclosed embodiment has a clear value as a monitor of rehydration therapy in a critical care setting.

In another embodiment of the present invention the water fraction, $f_w$ is estimated according to Equation (2) below, based on the measurement of reflectances, $R(\lambda)$ at three wavelengths and the empirically chosen calibration constants $c_0$, $c_1$ and $c_2$:

$$f_w = c_2 \log [R(\lambda_1)/R(\lambda_2)] + c_1 \log [R(\lambda_2)/R(\lambda_3)] + c_0 \qquad (2)$$

Better absolute accuracy can be attained using Equation (2) which incorporates reflectance measurements at an additional wavelength. The results of in vitro experiments on excised skin indicate that the wavelength triple ($\lambda_1=1190$ nm, $\lambda_2=1170$ nm, $\lambda_3=1274$ nm) yields accurate estimates of skin water content based on Equation (2).

In yet another embodiment of the present invention the water fraction, $f_w$ is estimated according to Equation (3) below, based on the measurement of reflectances, $R(\lambda)$ at three wavelengths and the empirically chosen calibration constants $c_0$ and $c_1$:

$$f_w = c_1 \frac{\log[R(\lambda_1)/R(\lambda_2)]}{\log[R(\lambda_3)/R(\lambda_2)]} + c_0 \qquad (3)$$

Figure 2:
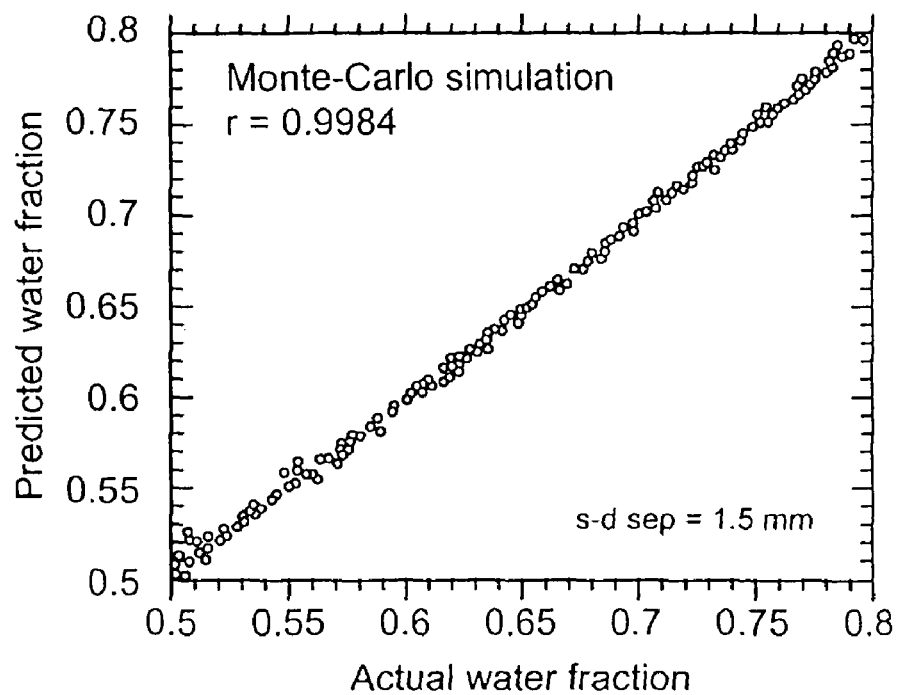
FIG. 2 is a graph showing an example regression for prediction of water from reflectances measured at three wavelengths.

Better absolute accuracy can be attained using Equations (3), as is attained using Equations (2), which also incorporates reflectance measurements at an additional wavelength. Numerical simulations as shown in FIG. 2 indicate that an accuracy better than ±0.5% can be achieved using Equation (3), with reflectances measured at three closely spaced wavelengths: $\lambda_1=1710$ nm, $\lambda_2=1730$ nm, and $\lambda_3=1740$ nm.

Individuals skilled in the art of near-infrared spectroscopy would recognize that, provided that the aforementioned guidelines are followed, additional terms can be added to Equations (1)-(3) to incorporate reflectance measurements made at more than three wavelengths and thus improve accuracy further.

Figure 3:
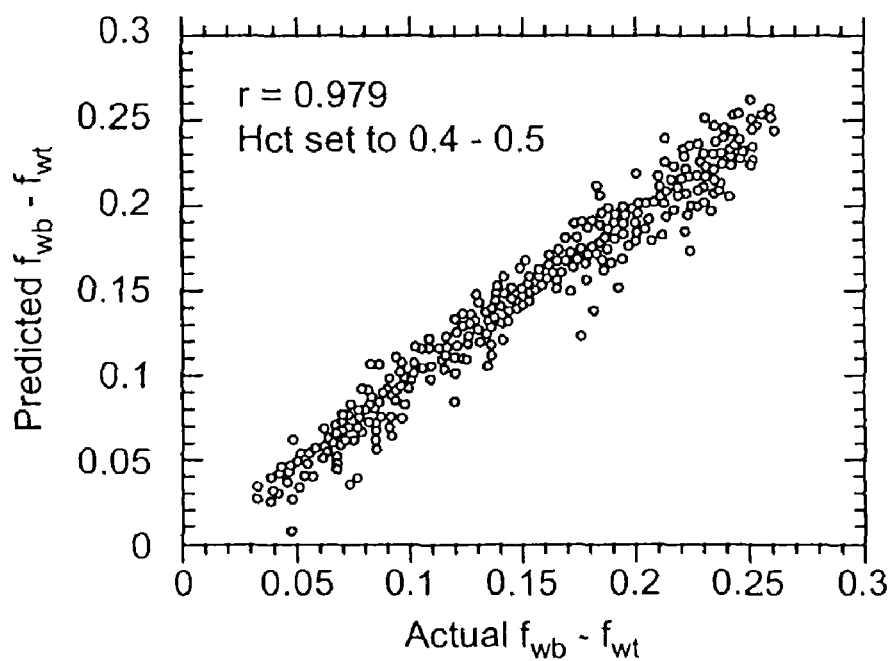
FIG. 3 is a graph showing an example regression of a two-wavelength algorithm for determination of the difference between the intravascular and extravascular water fraction from pulsatile reflectances measured two wavelengths.

An additional embodiment of the disclosed invention provides the ability to quantify shifts of fluid into and out of the bloodstream through a novel application of pulse spectrophotometry. This additional embodiment takes advantage of the observation that pulsations caused by expansion of blood vessels in the skin as the heart beats produce changes in the reflectance at a particular wavelength that are proportional to the difference between the effective absorption of light in the blood and the surrounding interstitial tissues. Numerical simulation indicate that, if wavelengths are chosen at which water absorption is sufficiently strong, the difference between the fractions of water in the blood, $f_w^{blood}$ and surrounding tissue, $f_w^{tissue}$ is proportional to the ratio of the dc-normalized reflectance changes ($\Delta R/R$) measured at two wavelengths, according to Equation (4) below:

$$f_w^{blood} - f_w^{tissue} = c_1 \left(\frac{\Delta R}{R}\right)_{\lambda_1} / \left(\frac{\Delta R}{R}\right)_{\lambda_2} + c_0, \quad (4)$$

where $c_0$ and $c_1$ are empirically determined calibration constants. This difference, integrated over time, provides a measure of the quantity of fluid that shifts into and out of the capillaries. FIG. 3 shows the prediction accuracy expected for the wavelength pair $\lambda_1=1320$ nm and $\lambda_2=1160$ nm.

Figure 4:
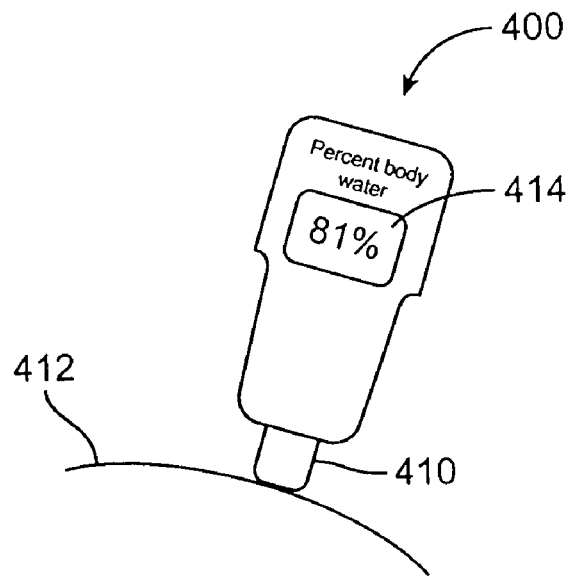
FIG. 4 is a diagram of an intermittent-mode version of a fluid monitor.
Figure 5:
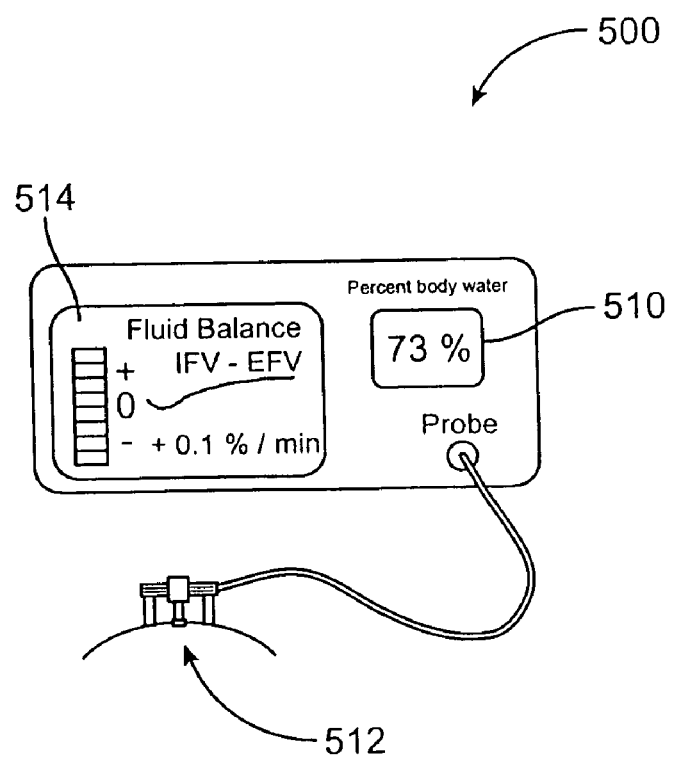
FIG. 5 is a diagram of a continuous-mode version of a fluid monitor.

FIGS. 4 and 5 show diagrams of two different versions of an instrument for measuring the amount of water in body tissues. The simplest version of the instrument 400 shown in FIG. 4 is designed for handheld operation and functions as a spot checker. Pressing the spring-loaded probe head 410 against the skin 412 automatically activates the display of percent tissue water 414. The use of the spring-loaded probe head provides the advantages of automatically activating the display device when needed and turning the device off when not in use, thereby extending device and battery life. Moreover, this unique use of a spring-loaded probe also provides the force needed to improve the reliability of measurements. Percent tissue water represents the absolute percentage of water in the skin beneath the probe (typically in the range 0.6-0.9). The force exerted by a spring or hydraulic mechanism (not shown) inside the probe head 410 pushes out most of the blood in the skin below the probe to reduce the error caused by averaging the intravascular and extravascular fluid fractions. A pressure transducer (not shown) within the probe head 410 measures the compressibility of the skin for deriving an index of the fraction of free (mobile) water.

The more advanced version of the fluid monitor 500 shown in FIG. 5 is designed for use as a critical-care monitor. In addition to providing a continuous display of the absolute volume fraction of water 510 at the site of measurement 512, it also provides a trend display of the time-averaged difference between the intravascular fluid volume ("IFV") and extravascular fluid volume ("EFV") fractions 514, updated every few seconds. This latter feature would give the physician immediate feedback on the net movement of water into or out of the blood and permit rapid evaluation of the effectiveness of diuretic or rehydration therapy. To measure the IFV-EFV difference, the monitor records blood pulses in a manner similar to a pulse oximeter. Therefore, placement of the probe on the finger or other well-perfused area of the body would be required. In cases in which perfusion is too poor to obtain reliable pulse signals, the IFV-EFV display would be blanked, but the extravascular water fraction would continue to be displayed. A mechanism for mechanically inducing the pulse is built into the probe to improve the reliability of the measurement of IFV-EFV under weak-pulse conditions.

Figure 6:
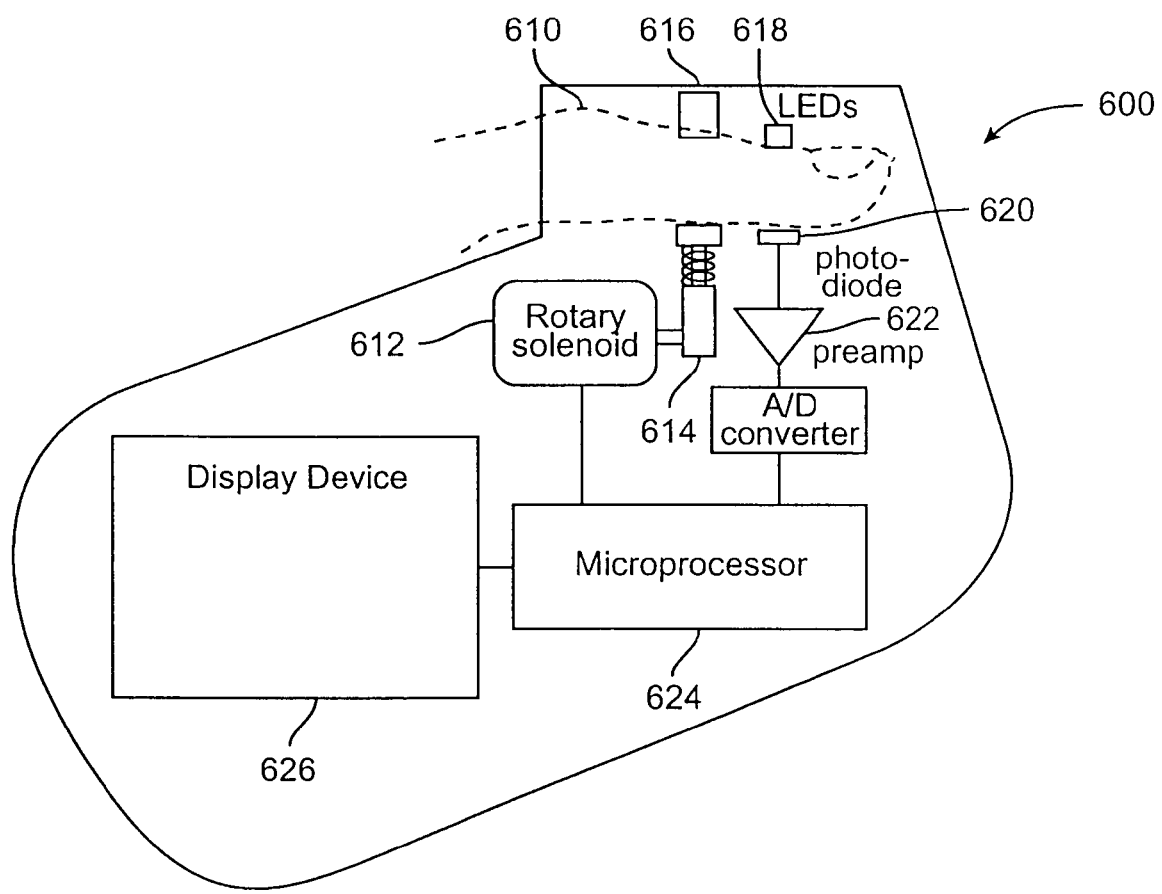
FIG. 6 is a block diagram of a handheld apparatus for noninvasive measurement and display of tissue water.

FIG. 6. is a block diagram of a handheld device 600 for measuring tissue water fraction within the IFV and the EFV, as well as shifts in water between these two compartments with a pulse inducing mechanism. Using this device 600, patient places his/her finger 610 in the probe housing. Rotary solenoid 612 acting through linkage 614 and collar 616 induces a mechanical pulse to improve the reliability of the measurement of IFV-EFV. LEDs 618 emit light at selected wavelengths and photodiode 620 measure the transmitted light. Alternately, the photodiode 620 can be placed adjacent to the LEDs to allow for the measurement of the reflectance of the emitted light. Preamplifier 622 magnifies the detected signal for processing by the microprocessor 624. Microprocessor 624, using algorithms described above, determines the tissue water fraction within the IFV and the EFV, as well as shifts in water between these two compartments, and prepares this information for display on display device 626. Microprocessor 624 is also programmed to handle the appropriate timing between the rotary solenoid's operation and the signal acquisition and processing. The design of the device and the microprocessor integrates the method and apparatus for reducing the effect of noise on measuring physiological parameters as described in U.S. Pat. No. 5,853,364, assigned to Nellcor Puritan Bennett, Inc., now a division of the assignee of the present invention, the entire disclosure of which is hereby incorporated herein by reference. Additionally, the design of the device and the microprocessor also integrates the electronic processor as described in U.S. Pat. No. 5,348,004, assigned to Nellcor Incorporated, now a division of the assignee of the present invention, the entire disclosure of which is hereby incorporated herein by reference.

As will be understood by those skilled in the art, other equivalent or alternative methods for the measurement of tissue water fraction within the IFV and the EFV, as well as shifts in water between these two compartments according to the embodiments of the present invention can be envisioned without departing from the essential characteristics thereof. For example, the device can be operated in either a handheld or a tabletop mode, and it can be operated intermittently or continuously. Moreover, individuals skilled in the art of near-infrared spectroscopy would recognize that additional terms can be added to the algorithms used herein to incorporate reflectance measurements made at more than three wavelengths and thus improve accuracy further. Also, light sources or light emission optics other then LED's including and not limited to incandescent light and narrowband light sources appropriately tuned to the desired wavelengths and associated light detection optics may be placed within the probe housing which is placed near the tissue location or may be positioned within a remote unit; and which deliver light to and receive light from the probe location via optical fibers. Additionally, although the specification describes embodiments functioning in a back-scattering or a reflection mode to make optical measurements of reflectances, other embodiments can be working in a forward-scattering or a transmission mode to make these measurements. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A device for determining body fluid-related metrics, the device comprising:
   a processing device configured to process a signal indicative of optical radiation received from a tissue location to compute the body fluid-related metrics, wherein the body fluid-related metrics comprise absolute volume fractions of water in extravascular and intravascular bodily tissue compartments and differences between intravascular fluid volume and extravascular fluid volume fractions.

2. The device of claim 1, comprising a display device coupled to the processing device and configured to display the body fluid-related metrics.

3. The device of claim 1, wherein the processing device receives and compares at least two sets of optical measurements, where the at least first set of optical measurements corresponds to the detection of the optical radiation whose absorption is primarily due to water, lipids and non-heme proteins, and where the at least second set of optical measurements corresponds to the detection of the optical radiation whose absorption is primarily due to water, and where a comparison of the at least two optical measurements provides a measure of the absolute water fraction within the tissue location.

4. The device of claim 1, wherein the processing device receives and compares at least two sets of optical measurements, where the at least two sets of optical measurements are based on the received optical radiation from at least two wavelengths and which are combined to form either a single ratio of the received optical radiation, a sum of ratios of the received optical radiation, or ratios of ratios of the received optical radiation.

5. The device of claim 1, wherein the processing device receives and compares at least two sets of optical measurements from at least two different wavelengths, where absorption of light at the at least two different wavelengths is primarily due to water which is in vascular blood and in extravascular tissue, and where a ratio of the at least two measurements provides a measure of a difference between fractions of water in the blood and the tissue location.

6. A device for determining body fluid-related metrics, the device comprising:
a processing device configured to process a signal indicative of optical radiation received from a tissue location to compute the body fluid-related metrics, the body fluid-related metrics comprising percent body water and a water balance, where the water balance is an integrated difference between a water fraction in blood and a water fraction in extravascular tissue.

7. A device for determining an absolute volume fraction of water within human tissue, the device comprising:
a processing device configured to process a signal indicative of optical radiation received from a tissue location to compute the absolute volume fraction of water, wherein the processing device receives and compares at least two sets of optical measurements, where the at least first set of optical measurements corresponds to the detection of the optical radiation whose absorption is primarily due to water, lipids and non-heme proteins, and where the at least second set of optical measurements corresponds to the detection of the optical radiation whose absorption is primary due to water, and where a comparison of the at least two optical measurements provides a measure of the absolute volume water fraction within the tissue location.

8. A device for determining a difference between an intravascular fluid volume and an extravascular fluid volume, the device comprising:
a processing device configured to process a signal indicative of optical radiation received from a tissue location to compute the difference between an intravascular fluid volume and an extravascular fluid volume, wherein the processing device receives and compares at least two sets of optical measurements from at least two different wavelengths, where absorption of light at the at least two different wavelengths is primarily due to water that is in vascular blood and in extravascular tissue, and where a comparison of the at least two measurements provides a measure of a difference between the fractions of water in the blood and the tissue location.

9. A method for determining body fluid-related metrics in a human tissue location, the method comprising:
processing a signal indicative of optical radiation received from the tissue location to compute the body fluid-related metrics via a processing device of a fluid monitor, wherein the body fluid-related metrics comprise absolute volume fractions of water in extravascular and intravascular bodily tissue compartments and differences between intravascular fluid volume and extravascular fluid volume fraction, wherein the processing comprises:
measuring at least two sets of optical measurements based on received optical radiation of at least two wavelengths;
combining the at least two sets of optical measurements to form either a single ratio of the received optical radiation, a sum of ratios of the received optical radiation, or ratios of ratios of the received optical radiation to form combinations of received optical radiation; and
determining the metrics from the combinations.

10. A device for determining body fluid-related metrics, the device comprising:
a processing device configured to process a signal indicative of optical radiation received from a tissue location to compute the body fluid-related metrics, wherein the optical radiation comprises a plurality of spectral wavelengths chosen to be preferentially absorbed by tissue water, non-heme proteins and lipids, where preferentially absorbed wavelengths are wavelengths whose absorption is substantially independent of individual concentrations of non-heme proteins and lipids, and is substantially dependent on a sum of the individual concentrations of non-heme proteins and lipids.

11. The device of claim 10, wherein the processing device is configured to process wavelengths chosen to ensure that the received optical radiation is substantially insensitive to scattering variations and such that the optical path lengths through a dermis portion of the tissue location at the wavelengths are substantially equal.

12. The device of claim 10, wherein the processing device is configured to process wavelengths chosen to ensure that the received optical radiation from the tissue location is insensitive to temperature variations, where the wavelengths are temperature isosbestic in the water absorption spectrum or individual wavelengths of the received optical radiation are combined in a way that substantially cancels temperature dependencies of the individual wavelengths of the received optical radiation when computing tissue water fractions.

13. The device of claim 10, wherein the processing device is configured to process wavelengths chosen from one of three primary bands of wavelengths of approximately 1100-1350 nm, approximately 1500-1800 nm, and approximately 2000-2300 nm.

14. The device of claim 10, wherein the processing device receives and compares at least two sets of optical measurements, where the at least first set of optical measurements corresponds to the detection of the optical radiation whose absorption is primarily due to water, lipids and non-heme proteins, and where the at least second set of optical measurements corresponds to the detection of the optical radiation whose absorption is primarily due to water, and where a comparison of the at least two optical measurements provides a measure of the absolute water fraction within the tissue location.

15. The device of claim 10, wherein the processing device receives and compares at least two sets of optical measurements, where the at least two sets of optical measurements are based on the received optical radiation from at least two wavelengths and which are combined to form either a single ratio of the received optical radiation, a sum of ratios of the received optical radiation, or ratios of ratios of the received optical radiation.

16. The device of claim 10, wherein the processing device receives and compares at least two sets of optical measurements from at least two different wavelengths, where absorption of light at the at least two different wavelengths is primarily due to water which is in vascular blood and in extravascular tissue, and where a ratio of the at least two measurements provides a measure of a difference between fractions of water in the blood and the tissue location.

17. The device of claim 10, wherein the processing device is configured to compute body fluid-related metrics that comprise a tissue water fraction, where the tissue water fraction ($f_w$) is determined such that $$f_w = c_1 \log [R(\lambda_1)/R(\lambda_2)] + c_0, \text{ and where:}$$

calibration constants $c_0$ and $c_1$ are chosen empirically $R(\lambda_1)$ is the received optical radiation at a first wavelength; and $R(\lambda_2)$ is the received optical radiation at a second wavelength.

18. The device of claim 17, wherein the processing device is configured to process first and second wavelengths that are approximately 1300 nm and approximately 1168 nm, respectively.

19. The device of claim 17, wherein the processing device is configured to process first and second wavelengths that are approximately 1230 nm and approximately 1168 nm, respectively.

20. The device of claim 10, wherein the processing device is configured to compute body fluid-related metrics that comprise a tissue water fraction, and where the tissue water fraction ($f_w$) is determined such that $$f_w = c_2 \log [R(\lambda_1)/R(\lambda_2)] + c_1 \log [R(\lambda_2)/R(\lambda_3)] + c_0, \text{ and where:}$$

calibration constants $c_0$, $c_1$ and $c_2$ are chosen empirically;

$R(\lambda_1)$ is the received optical radiation at a first wavelength;

$R(\lambda_2)$ is the received optical radiation at a second wavelength; and $R(\lambda_3)$ is the received optical radiation at a third wavelength.

21. The device of claim 10, wherein the processing device is configured to process first, second and third wavelengths that are approximately 1190 nm, approximately 1170 nm and approximately 1274 nm, respectively.

22. The device of claim 10, wherein the processing device is configured to compute body fluid-related metrics that comprise a tissue water fraction, and where the tissue water fraction ($f_w$) is determined such that $$f_w = c_1 \frac{\log[R(\lambda_1)/R(\lambda_2)]}{\log[R(\lambda_3)/R(\lambda_2)]} + c_0,$$

and where:

calibration constants $c_0$ and $c_1$ are chosen empirically;

$R(\lambda_1)$ is the received optical radiation at a first wavelength;

$R(\lambda_2)$ is the received optical radiation at a second wavelength; and $R(\lambda_3)$ is the received optical radiation at a third wavelength.

23. The device of claim 22, wherein the processing device is configured to process first, second and third wavelengths that are approximately 1710 nm, approximately 1730 nm and approximately 1740 nm, respectively.

24. The device of claim 10, wherein the processing device is configured to compute body fluid-related metrics that comprise a quantified measure of a difference between a water fraction in blood and a water fraction in extravascular tissue, where the difference is determined such that $$f_w^{blood} - f_w^{tissue} = c_1 \left(\frac{\Delta R}{R}\right)_{\lambda_1} \bigg/ \left(\frac{\Delta R}{R}\right)_{\lambda_2} + c_0,$$

and where:

$f_w^{blood}$ is the water fraction in the blood;

$f_w^{tissue}$ is the water fraction in the extravascular tissue;

calibration constants $c_0$ and $c_1$ are chosen empirically; and $$\left(\frac{\Delta R}{R}\right)_{\lambda_1} \bigg/ \left(\frac{\Delta R}{R}\right)_{\lambda_2}$$

is a ratio of dc-normalized received optical radiation changes at a first wavelength, $\lambda_1$ and a second wavelength, $\lambda_2$ respectively, where the received optical radiation changes are caused by a pulsation caused by expansion of blood vessels in tissue.

25. The device of claim 24, wherein the processing device is configured to compute body fluid metrics that comprise an integral of the difference between the water fraction in the blood and the water fraction in the extravascular tissue to provide a measure of water that shifts into and out of capillaries in the tissue location.

26. The device of claim 24, wherein the processing device is configured to process first and second wavelengths that comprise approximately 1320 nm and approximately 1160 nm, respectively.

27. A device for determining body fluid-related metrics, the device comprising:

a processing device configured to process a signal indicative of optical radiation received from a tissue location to compute the body fluid-related metrics, wherein the body fluid-related metrics comprises a tissue water fraction, and where the tissue water fraction ($f_w$) is determined such that $$f_w = c_1 \frac{\log[R(\lambda_1)/R(\lambda_2)]}{\log[R(\lambda_3)/R(\lambda_2)]} + c_0$$

and where:
  calibration constants $c_0$ and $c_1$ are chosen empirically;
  $R(\lambda_1)$ is the received optical radiation at a first wavelength;
  $R(\lambda_2)$ is the received optical radiation at a second wavelength; and
  $R(\lambda_3)$ is the received optical radiation at a third wavelength.

28. The device of claim 27, wherein the processing device is configured to process wavelengths chosen to ensure that the received optical radiation is substantially insensitive to scattering variations and such that the optical path lengths through a dermis portion of the tissue location at the wavelengths are substantially equal.

29. The device of claim 27, wherein the processing device is configured to process wavelengths chosen to ensure that the received optical radiation from the tissue location is substantially insensitive to temperature variations, where the wavelengths of the optical radiation are temperature isosbestic in the water absorption spectrum or where the wavelengths of the received optical radiation are combined in a way that substantially cancels temperature dependencies of individual wavelengths of the received optical radiation when computing tissue water fractions.

30. The device of claim 27, wherein the processing device is configured to process wavelengths chosen from one of three primary bands of wavelengths of approximately 1100-1350 nm, approximately 1500-1800 nm, and approximately 2000-2300 nm.

31. The device of claim 27, wherein the processing device receives and compares at least two sets of optical measurements, where the at least first set of optical measurements corresponds to the detection of the received optical radiation whose absorption is primarily due to water, lipids and non-heme proteins, and where the at least second set of optical measurements corresponds to the detection of the received optical radiation whose absorption is primarily due to water, and where a comparison of the at least two optical measurements provides a measure of the absolute water fraction within the tissue location.

32. The device of claim 27, wherein the processing device is configured to process first, second and third wavelengths that are approximately 1710 nm, approximately 1730 nm and approximately 1740 nm, respectively.

33. A device for determining body fluid-related metrics, the device comprising:
  a processing device configured to process a signal indicative of optical radiation received from a tissue location to compute the body fluid-related metrics, wherein received optical radiation comprises a plurality of spectral wavelengths chosen to ensure that the computed body fluid-related metrics are substantially insensitive to scattering variations and such that the optical path lengths through the tissue location at the wavelengths are substantially equal.

34. The device of claim 33, wherein the processing device is configured to process wavelengths chosen to ensure that the received optical radiation from the tissue location is substantially insensitive to temperature variations, where wavelengths of the received optical radiation are temperature isosbestic in the water absorption spectrum, or where wavelengths of the received optical radiation are combined in a way that substantially cancel temperature dependencies of any individual wavelength of the received optical radiation when computing tissue water fractions.

35. The device of claim 33, wherein the processing device is configured to process wavelengths of the received optical radiation are chosen from one of three primary bands of wavelengths of approximately 1100-1350 nm, approximately 1500-1800 nm, and approximately 2000-2300 nm.

36. The device of claim 33, wherein the processing device receives and compares at least two sets of optical measurements, where the at least first set of optical measurements corresponds to the detection of the received optical radiation whose absorption is primarily due to water, lipids and non-heme proteins, and where the at least second set of optical measurements corresponds to the detection of the received optical radiation whose absorption is primarily due to water, and where a comparison of the at least two optical measurements provides a measure of the absolute water fraction within the tissue location.

37. The device of claim 33, wherein the processing device receives and compares at least two sets of optical measurements, where the at least two sets of optical measurements are based on the received optical radiation from at least two wavelengths and which are combined to form either a single ratio of the received optical radiation, a sum of ratios of the received optical radiation, or ratios of ratios of the received optical radiation.

38. The device of claim 33, wherein the processing device is configured to compute body fluid-related metrics that comprise a tissue water fraction, and where the tissue water fraction ($f_w$) is determined such that $f_w = c_1 \log [R(\lambda_1)/R(\lambda_2)] + c_0$, and where:

calibration constants $c_0$ and $c_1$ are chosen empirically;
  $R(\lambda_1)$ is the received optical radiation at a first wavelength; and
  $R(\lambda_2)$ is the received optical radiation at a second wavelength.

39. The device of claim 38, wherein the processing device is configured to process first and second wavelengths that are approximately 1300 nm and approximately 1168 nm, respectively.

40. The device of claim 38, wherein the processing device is configured to process first and second wavelengths that are approximately 1230 nm and approximately 1168 nm, respectively.

41. The device of claim 33, wherein the processing device is configured to compute body fluid-related metrics that comprise a tissue water fraction, and where the tissue water fraction ($f_w$) is determined such that $f_w = c_2 \log [R(\lambda_1)/R(\lambda_2)] + c_1 \log [R(\lambda_2)/R(\lambda_3)] + c_0$, and where:

calibration constants $c_0$, $c_1$ and $c_2$ are chosen empirically;
  $R(\lambda_1)$ is the received optical radiation at a first wavelength;
  $R(\lambda_2)$ is the received optical radiation at a second wavelength; and
  $R(\lambda_3)$ is the received optical radiation at a third wavelength.

42. The device of claim 41, wherein the processing device is configured to process first, second and third wavelengths that are approximately 1190 nm, approximately 1170 nm, and approximately 1274 nm, respectively.

43. A device for determining body fluid-related metrics, the device comprising:
  a processing device configured to process a signal indicative of optical radiation received from a tissue location compute the body fluid-related metrics, wherein the received optical radiation comprises a plurality of spectral wavelengths chosen to ensure that the received optical radiation from the tissue location is substantially insensitive to temperature variations, wherein wavelengths of the received optical radiation are temperature isosbestic in the water absorption spectrum or wherein the signal is processed in such a way that temperature dependencies of individual wavelengths of the received optical radiation is substantially cancelled when computing tissue water fractions.

44. The device of claim 43, wherein the processing device is configured to process wavelengths chosen from one of three primary bands of wavelengths of approximately 1100-1350 nm, approximately 1500-1800 nm, and approximately 2000-2300 nm.

45. The device of claim 43, wherein the processing device receives and compares at least two sets of optical measurements, where the at least first set of optical measurements corresponds to the detection of optical radiation whose absorption is primarily due to water, lipids and non-heme proteins, and where the at least second set of optical measurements corresponds to the detection of optical radiation whose absorption is primarily due to water, and where a comparison of the at least two optical measurements provides a measure of the absolute water fraction within the tissue location.

46. The device of claim 43, wherein the processing device receives and compares at least two sets of optical measurements, where the at least two sets of optical measurements are based on the received optical radiation from at least two wavelengths and which are combined to form either a single ratio of the received optical radiation, a sum of ratios of the received optical radiation, or ratios of ratios of the received optical radiation.

47. The device of claim 43, wherein the processing device is configured to compute body fluid-related metrics that comprise a tissue water fraction, and where the tissue water fraction ($f_w$) is determined such that $$f_w = c_1 \log [R(\lambda_1)/R(\lambda_2)] + c_0, \text{ and where:}$$

calibration constants $c_0$ and $c_1$ are chosen empirically;
$R(\lambda_1)$ is the received optical radiation at a first wavelength; and
$R(\lambda_2)$ is the received optical radiation at a second wavelength.

48. The device of claim 47, wherein the processing device is configured to process first and second wavelengths that are approximately 1300 nm and approximately 1168 nm, respectively.

49. The device of claim 47, where the processing device is configured to process first and second wavelengths that are approximately 1230 nm and approximately 1168 nm, respectively.

50. The device of claim 43, wherein the processing device is configured to compute body fluid-related metrics that comprise a tissue water fraction, and where the tissue water fraction ($f_w$) is determined such that $$f_w = c_2 \log [R(\lambda_1)/R(\lambda_2)] + c_1 \log [R(\lambda_2)/R(\lambda_3)] + c_0, \text{ and where:}$$

calibration constants $c_0$, $c_1$ and $c_2$ are chosen empirically;
$R(\lambda_1)$ is the received optical radiation at a first wavelength;
$R(\lambda_2)$ is the received optical radiation at a second wavelength; and
$R(\lambda_3)$ is the received optical radiation at a third wavelength.

51. The device of claim 50, wherein the processing device is configured to process first, second and third wavelengths that are approximately 1190 nm, approximately 1170 nm, and approximately 1274 nm, respectively.

* * * * *